US009511045B2

(12) United States Patent
Busserolles et al.

(10) Patent No.: US 9,511,045 B2
(45) Date of Patent: Dec. 6, 2016

(54) USE OF RILUZOLE FOR TREATING OR PREVENTING THE ADVERSE EFFECTS OF ANTINEOPLASTIC AGENTS

(75) Inventors: Jérôme Busserolles, Saulzet (FR); Abdelkrim Alloui, Clermont Ferrand (FR); Michel Lazdunski, Nice (FR); Alain Eschalier, Chamalieres (FR)

(73) Assignee: UNIVERSITE D'AUVERGNE CLERMONT I, Clermont Ferrand (FR)

( * ) Notice: Subject to any disclaimer, the term of this patent is extended or adjusted under 35 U.S.C. 154(b) by 50 days.

(21) Appl. No.: 13/582,178

(22) PCT Filed: Mar. 2, 2011

(86) PCT No.: PCT/FR2011/050432
§ 371 (c)(1),
(2), (4) Date: Nov. 28, 2012

(87) PCT Pub. No.: WO2011/107710
PCT Pub. Date: Sep. 9, 2011

(65) Prior Publication Data
US 2013/0064775 A1 Mar. 14, 2013

(30) Foreign Application Priority Data

Mar. 2, 2010 (FR) ...................................... 10 51491

(51) Int. Cl.
*A61K 31/428* (2006.01)
*A61K 31/44* (2006.01)
*A61K 31/282* (2006.01)
*A61K 45/06* (2006.01)
*A61K 49/00* (2006.01)

(52) U.S. Cl.
CPC ........... *A61K 31/282* (2013.01); *A61K 31/428* (2013.01); *A61K 45/06* (2013.01); *A61K 49/0008* (2013.01); *A01K 2227/105* (2013.01); *A01K 2267/0331* (2013.01)

(58) Field of Classification Search
CPC ..... A61K 49/00; A61K 31/428; A61K 31/44
USPC ........... 424/133.1, 138.1; 514/346, 350, 367, 514/479
See application file for complete search history.

(56) References Cited

U.S. PATENT DOCUMENTS

| 4,536,386 | A | 8/1985 | Keenan | |
| 5,624,945 | A | 4/1997 | Bousseau et al. | |
| 7,772,220 | B2 * | 8/2010 | Yoo | 514/171 |
| 2002/0151465 | A1 | 10/2002 | Messing et al. | |
| 2006/0188445 | A1 | 8/2006 | Ou et al. | |
| 2008/0124333 | A1 * | 5/2008 | Goydos | A61K 31/27 424/138.1 |
| 2008/0234339 | A1 * | 9/2008 | Weiss | A61K 31/136 514/367 |
| 2010/0221246 | A1 * | 9/2010 | Goydos et al. | 424/133.1 |

FOREIGN PATENT DOCUMENTS

| WO | 00/28992 A1 | 5/2000 |
| WO | 00/66121 A1 | 11/2000 |
| WO | WO -00/66121 * | 11/2000 |
| WO | 2006/099739 A1 | 9/2006 |
| WO | 2009/028605 A1 | 3/2009 |

OTHER PUBLICATIONS

Mattieu J. Guitton et al. New Pharmacological Strategies to Restore Hearing and Treat Tinnitus, Acta Otolaryngol 2004, 124, 411-415.*
T.J. Coderre et al. A Comparison of the glutamate release inhibition and anti-allodynic effects of gabapentin, lamotrigine, and riluzole in a model of neuropathic pain, Journal of Neurochemistry, 2007, 100, 1289-1299.*
Toshio Narahashi, Neuroreceptors and Ion Channels as the Basis for Drug Action: Past, Present, and Future, The Journal of Pharmacology and Experimental Therapeutics, 294, 1-26, 2000.*
Abstracts of the Annual Meeting of the Society for Neuroscience Society for Neuroscience, Washington D.C. (US), Effects of Pretreatment with anti-convulsant agents on the development of nerve-induced mechanical and fold hpersensitivity, vol. 26(1-2), p. 1216, 2000.*
Todd, et al., "Inhibition of transcription by platinum antitumor compounds", Metallomics: Integrated Biometal Science 2009 LKND-PUBMED:20046924, vol. 1, No. 4, 2009, pp. 280-291, XP002636711.
Lefebvre, et al., "Effects of pretreatment with anti-convulsant agents on the development of nerve injury-induced mechanical and cold hypersensitivity", Abstracts of the Annual Meeting of the Society for Neuroscience, Society for Neuroscience, Washington, DC, US, vol. 26, No. 1-2, Jan. 1, 2000, p. 1216, XP008136024.
Hernandez, et al., "The Modulation of Prostate Cancer Risk With alpha-Tocopherol: A Pilot Randomized, Controlled Clinical Trial", Journal of Urology, Lippincott Williams & Wilkins, Baltimore, MD, US LNKD-DOI:10.1097/01.JU.0000165151.08560.6A, vol. 174, No. 2, Aug. 1, 2005, pp. 519-522, XP025378144.

(Continued)

*Primary Examiner* — Michael G Hartley
*Assistant Examiner* — Jagadishwar Samala
(74) *Attorney, Agent, or Firm* — Knobbe, Martens, Olson & Bear, LLP

(57) ABSTRACT

This invention relates to riluzole for use in the treatment or prevention of adverse effects associated with the administration of anticancer agents having neurotoxic effects, such as, for example, platinum salts, taxanes and periwinkle alkaloids.

19 Claims, 2 Drawing Sheets

(56) References Cited

OTHER PUBLICATIONS

Authier, et al., "Assessment of allodynia and hyperalgesia after cisplatin administration to rats", Neuroscience Letters, vol. 291, No. 2, Sep. 15, 2000, pp. 73-76, XP002599724.
International Search Report issued on May 25, 2011 for International Application No. PCT/FR2011/050432.
Hoggarth, Eric. "The preparation and reactivity of some 2-methanesulphonyl-benzazoles." J. Chem. Soc. (1949): 3311-3315.
Mita, C., et al. "Phase I and pharmacological study of an oxaliplatin and carboplatin combination in advanced malignancies." Annals of oncology 14 (2003): 1776-1782.
Ding, H., et al. "Inhibitory effect of methylmercury on proliferation of human small cell lung cancer cells." Department of Respiration, The First Hospital of Jilin University, Changchun, China. 2009.
Xin, X., et al. "Effects of Dextromethorphan and Riluzole on Neurotoxicity and Oxidative Damage of Rats Induced by Methylmercury." The 3rd Academic Annual Conference of China Preventive Medicine Association/The 1st WFPHA Public Hygiene Conference in APAC/The 5th Annual Conference of Global Chinese Association of Public Hygiene. Shenyang, Liaoning. Oct. 26, 2009.
Descoeur J., et al. "Oxaliplatin-induced cold hypersensitivity is due to remodeling of ion channel expression in nociceptors." EMBO Mol. Med. May 2011, vol. 3, No. 5, pp. 266-278.
Adelsberger et al., "The chemotherapeutic oxaliplatin alters voltage-gated Na$^+$channel kinetics on rat sensory neurons," European Journal of Pharmacology, 2000, vol. 406: p. 25-32.
Authier et al., "Pain related behavior during vincristine-induced neuropathy in rats," NeuroReport, 1999, vol. 10: p. 965-968.
Benoit et al., "Oxaliplatin, an Anticancer Agent that Affects both Na+ and K+ Channels in Frog Peripheral Myelinated Axons," Gen. Phys. Biophys., 2006, vol. 25: p. 263-276.
Brooks et al., "Tests to assess motor phenotype in mice: a user's guide," Nature Reviews Neuroscience, Jul. 2009, vol. 10: p. 519529.
de Gramont et al., "Leucovorin and fluorouracil with or without oxaliplatin as first-line treatment in advanced colorectal cancer," J Clin Oncol, Aug. 2000, 18 (16): p. 2938-47. Abstract Only.
Dimitrov et al., "A Possible Link of Oxaliplatin-Induced Neuropathy With Potassium Channel Deficit," Muscle Nerve, 2012, vol. 45: p. 403-411.
Fraser et al., "Drug and chemical metabolites in clinical toxicology investigations: The importance of ethylene glycol, methanol and cannabinoid metabolite analyses," Clinical Biochemistry, 2002, vol. 35: p. 501-511.
Garrido et al. "Nuevas alternativas en el tratamiento del cancer gástrico avanzado," Rev. Méd Chile, 2007, vol. 135: p. 1380-1387.
Gauchan et al., "Involvement of increased expression of transient receptor potential melastatin 8 in oxaliplatin-induced cold allodynia in mice," Neuroscience Letters, 2009, vol. 458: p. 93-95.
Gill et al, "Cisplatin-Induced Apoptosis in Rat Dorsal Root Ganglion Neurons Is Associated with Attempted Entry into the Cell Cycle," The Journal of Clinical Investigation, Jun. 1998, vol. 101(12): p. 2842-2850.
Gourley et al., "Antidepressant-like properties of oral riluzole and utility of incentive disengagement models of depression in mice," Psychopharmacology, 2012, vol. 219: p. 805-814.
Graham et al., "Clinical Pharmacokinetics of Oxaliplatin: A Critical Review," Clinical Cancer Research, Apr. 2000, vol. 6: p. 1205-1218.
Gregg et al., "Cisplatin neurotoxicity: the relationship between dosage, time, and platinum concentration in neurologic tissues, and morphologic evidence of toxicity," J Clin Oncol, May 1992, vol. 10(5): p. 795-803. Abstract Only.
Grolleau et al., "A Possible Explanation for a Neurotoxic Effect of the Anticancer Agent Oxaliplatin on Neuronal Voltage-Gated Sodium Channels," The American Physiological Society, 2001, p. 2293-2297.
Grothey, A. "Clinical management of oxaliplatin-associated neurotoxicity," Clin Colorectal Cancer, Apr. 2005, vol. 5 Suppl 1: p. S38-46. Abstract Only.
Haller, "Safety of Oxaliplatin in the Treatment of Colorectal Cancer," Cancer Network, Dec. 2000, Review Article 1: p. 1-5.
Holmes et al., "Comparative Neurotoxicity of Oxaliplatin, Cisplatin, and Ormaplatin in a Wistar Rat Model," Toxicological Sciences, 1998, vol. 46: p. 342-351.
Ip et al., "Differential expression of ATP7A, ATP7B and CTR1 in adult rat dorsal root ganglion tissue," Molecular Pain, 2010, vol. 6(53): p. 1-10.
Jaggi et al., "Mechanisms in cancer-chemotherapeutic drugs-induced peripheral neuropathy," Toxicology, 2012, vol. 291: p. 1-9.
Jong et al., "Oxaliplatin Transport Mediated by Organic Cation/Carnitine Transporters OCTN1 and OCTN2 in Overexpressing Human Embryonic Kidney 293 Cells and Rat Dorsal Root Ganglion Neurons," The Journal of Pharmacology and Experimental Therapeutics, 2011, vol. 338(2): p. 537-547.
Joseph et al., "Comparison of Oxaliplatin- and Cisplatin-Induced Painful Peripheral Neuropathy in the Rat," The Journal of Pain, 2009, vol. 10(5): p. 534-541.
Kagiava et al., "The effects of oxaliplatin, an anticancer drug, on potassium channels of the peripheral myelinated nerve fibres of the adult rat," NeuroToxicity, 2008, vol. 29: p. 1100-1106.
Kawashiri et al., "L type $Ca^{2+}$ channel blockers prevent oxaliplatin-induced cold hyperalgesia and TRPM8 overexpression in rats," Molecular Pain, 2012, vol. 8(7): p. 1-10.
Luong et al., "Assessment of Motor Balance and Coordination in Mice using the Balance Beam," Journal of Visualized Experiments, 2011, vol. 49: p. 1-3.
McDonald et al., "Cisplatin preferentially binds to DNA in dorsal root ganglion neurons in vitro and in vivo: a potential mechanism for neurotoxicity," Neurobiology of Disease, 2005, vol. 18: p. 305-313.
Moser et al., "A Dominant Mutation That Predisposes to Multiple Intestinal Neoplasia in the Mouse," Science, Jan. 1990, vol. 247, p. 322-324.
Pereira et al., "Role of the TREK2 potassium channel in cold and warm thermosensation and in pain perception," PAIN, 2014, p. 1-11.
Podratz et al., "Cisplatin induced Mitochondrial DNA damage in dorsal root ganglion neurons," Neurobiology of Disease, 2011, vol. 41: p. 661-668.
Schulze et al., "Prolonged Oxaliplatin Exposure Alters Intracellular Calcium Signaling: A New Mechanism to Explain Oxaliplatin-Associated Peripheral Neuropathy," Clinical Colorectral Cancer, 2011, vol. 10(2): p. 126-133.
Shoemaker et al., "N-Ethyl-N-nitrosourea Treatment of Multiple Intestinal Neoplasia (Min) Mice: Age-related Effects on the Formation of Intestinal Adenomas, Cystic Crypts, and Epidermoid Cysts," Cancer Research, Oct. 1995, vol. 55: p. 4479-4485.
Ta et al., "Neurotoxicity of oxaliplatin and cisplatin for dorsal root ganglion neurons correlates with platinum—DNA binding," NeuroToxicology, 2006, vol. 27: p. 992-1002.
Warwick et al., "The contribution of satellite glial cells to chemotherapy-induced neuropathic pain," European Journal of Pain, 2013, vol. 17: p. 571-580.
Webster et al., "Oxaliplatin induces hyperexcitability at motor and autonomic neuromuscular junctions through effects on voltage-gated sodium channels," British Journal of Pharmacology, 2005, vol. 146: p. 1027-1039.
Yoon et al., "Spinal Astrocyte Gap Junctions Contribute to Oxaliplatin-Induced Mechanical Hypersensitivity," The Journal of Pain, 2013, vol. 14(2): p. 205-214.
Zhao et al., "Acute cold hypersensitivity characteristically induced by oxaliplatin is caused by the enhanced responsiveness of TRPA1 in mice," Molecular Pain, 2012, vol. 8(55): p. 1-11.

\* cited by examiner

USE OF RILUZOLE FOR TREATING OR PREVENTING THE ADVERSE EFFECTS OF ANTINEOPLASTIC AGENTS

CROSS REFERENCE TO RELATED APPLICATIONS

This application is the U.S. National Phase of International Application No. PCT/FR2011/050432, filed Mar. 2, 2011, designating the U.S. and published as WO 2011/107710 on Sep. 9, 2011 which claims the benefit of French Patent Application No. 10 51491 filed Mar. 2, 2010.

This invention relates to riluzole for use in the treatment or prevention of adverse effects associated with the administration of anticancer agents having neurotoxic affects, such as, for example, platinum salts, taxanes and periwinkle alkaloids.

Riluzole

Riluzole, which is sold by Aventis under the name Rilutek®, is currently indicated for extending the lifetime or delaying the use of assisted mechanical ventilation in patients with amyotrophic lateral sclerosis (Miller et al. Neurology 2009 73: 1218-26).

Oxaliplatin

Oxaliplatin is an antineoplastic cytotoxic compound, comprised of a platinum atom complexed with a 1,2-diaminohexane (DACH) and an oxalate group. It is used, among other things, in the treatment of colorectal cancers. It has recently been used in the treatment of advanced-stage metastatic colorectal cancer (Baker, Rev Gastroenterol Disord. 2003 3: 31-8; Screnci et al., Br J Cancer 2000 82: 966-72) and has also shown an activity in other cancers: ovarian, breast, lung (Muggia, Semin Oncol. 2004 31: 17-24; Petit et al., Anticancer Drugs. 2006 17: 337-43). Neurotoxicity is a common adverse effect of this molecule and this effect often occurs in two forms: acute and chronic.

Acute neurotoxicity is characterized by the rapid onset of distal dysesthesia induced by cold with or without paresthesia (Gamelin et al., Semin Oncol. 2002 29: 21-33; Lehky et al., Muscle Nerve. 2004 29: 387-92), and muscular disorders: myotonia, cramps, prolonged muscle fasciculations affecting the legs, the hands and the jaws and inhibiting movement (Grolleau et al., J Neurophysiol. 2001 85: 2293-7). Around 85% to 95% of patients treated develop these symptoms, which begin during infusion and persist for the first 24 to 48 hours.

The intensity of this acute neurotoxicity is dependent on plasma concentrations of oxaliplatin, and it is therefore suitable for preventing concentration peaks. (Grothey, Clin Colorectal Cancer. 2005 5: S38-S46). The resolution of symptoms occurs within around one week, but the symptoms reappear in the next infusion. By comparison with the other platinum-derived agents, the neurotoxic profile of oxaliplatin is particular due to this acute neurotoxicity. In patients with such acute symptoms, studies have shown little or no axonal degeneration, suggesting a specific effect of oxaliplatin on the sensory neurons and the motor neurons. The intensity of the problems observed and in particular the hypersensitivity to cold, after the first treatments, is a marker of neurotoxicity.

Chronic and cumulative peripheral neurotoxicity is considered to be the dose-limiting adverse effect of oxaliplatin and may result in interruption of the treatment. The neurotoxicity is manifested by symptoms capable of including a peripheral sensory neuropathy, sensory impairment, sensory ataxia and/or a fine sensorimotor coordination deficit. The neuropathy develops progressively in approximately 10 to 15% of patients after a cumulative dose of 780 to 850 mg/m2, corresponding to approximately six cycles at a dose of 85 mg/m2 (Gamelin et al., Semin Oncol. 2002 29: 21-33). Peripheral sensory neuropathy appears in the form of distal dysesthesias and paresthesias (hands, feet, toes), with a loss of sensation. Sensory neuropathy, sensory ataxia and/or fine sensorimotor coordination deficit cause problems with writing, holding objects, etc. The development of sensory neuropathy is correlated with the cumulative oxaliplatin dose (Wilson et al., J Clin Oncol. 2002 20: 1767-74).

Animal studies have made it possible to develop a neurotoxicity model induced by a single infusion of oxaliplatin with the main symptoms seen in humans, in particular hypersensitivity to cold (Ling et al., Toxicology. 2007 234: 176-84; Ling et al., Pain. 2007 128: 225-34).

More generally, neurotoxicity is an adverse effect common to numerous anticancer agents. Thus, taxanes and vincristine induce neuropathy in humans (Quastoff and Hartung, J Neurol. 2002 249: 9-17; Stillman and Cata, Curr Pain Headache Rep. 2006 18: 321-324; Park et al., Curr Med. Chem. 2008 15: 3081-3094).

There is therefore a need for compounds capable of treating or preventing adverse effects caused by anticancer agents, in particular anticancer agents inducing neurotoxicity.

DESCRIPTION OF THE INVENTION

It has been found that riluzole enables the appearance of adverse effects associated with the administration of oxaliplatin to be prevented.

More specifically, the inventors evaluated the potential of riluzole to reduce cold hypersensitivity phenomena. In an animal model, it was found that riluzole is capable of correcting cold hypersensitivity induced by oxaliplatin. This important effect leads us to expect a beneficial action of riluzole on all sensory symptoms, in particular neurotoxicity, observed during administration of oxaliplatin in humans.

Therefore, a first aspect of the invention concerns a compound of formula (I):

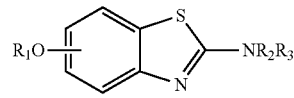

in which:
R1 is chosen from a hydrogen atom, a C1-C6 alkyl group and a C1-C6 halogenoalkyl group;
R2, R3, identical or different, are chosen from a hydrogen atom or a C1-C6 alkyl group C1-C6, as well as the pharmaceutically acceptable salts of this compound, for use in the treatment or prevention of an adverse effect, in particular neurotoxicity, induced by an anticancer agent.

The present invention also relates to the use of such a compound of formula (I) for the production of a drug for the treatment or prevention of an adverse effect, in particular neurotoxicity, induced by an anticancer agent.

R1 may, for example, be a halogenoalkyl group, preferably per-halogenoalkyl. Preferably, R1 is a perfluoroalkyl group, such as trifluoromethyl.

R2 and/or R3 can, for example, be a hydrogen atom.

In a particular embodiment, the compound of formula (I) is characterized in that it is the compound of formula (II):

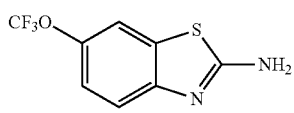

or a pharmaceutically acceptable salt of this compound of formula (II).

According to this invention, the alkyl radicals represent saturated hydrocarbon radicals, with a straight or branched chain, of 1 to 6 carbon atoms, preferably 1 to 4 carbon atoms. It is possible in particular to cite, when they are linear, methyl, ethyl, propyl, butyl, pentyl and hexyl radicals. It is possible in particular to cite, when they are branched or substituted by one or more alkyl radicals, the isopropyl, tert-butyl, 2-methylbutyl, 2-methylpentyl, and 1-methylpentyl radicals.

The halogenoalkyl radicals according to this invention include alkyl radicals as defined above in which one or more hydrogen atoms are substituted by a halogen atom (fluorine, chlorine, bromine, iodine), in particular by a chlorine or fluorine atom. The halogenoalkyls can be per-halogenoalkyl radicals, i.e. halogenoalkyl radicals in which all of the hydrogen atoms are substituted by a halogen atom, in particular per-fluoroalkyl radicals of formula $C_nF_{2n+1}$, in which n represents a whole number between 1 and 6. As an example of a per-fluoroalkyl group, it is possible to cite in particular trifluoromethyl.

The adverse effects, in particular neurotoxicity, can be treated at any stage. By "treatment", we mean a curative treatment (intended to relieve, slow or stop the adverse effects). By "prevention", we mean a prophylactic treatment (intended to reduce the risk of appearance of adverse effects).

The term "pharmaceutically acceptable salt" refers to relatively non-toxic, inorganic and organic acid addition salts of the compounds of the present invention. These salts can be prepared in situ during the final isolation and purification of the compounds. In particular, the acid addition salts can be prepared by separately reacting the purified compound in its purified form with an organic or inorganic acid and by isolating the salt thus formed. Among the examples of acid addition salts are the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, lactobionate, sulfamates, malonates, salicylates, propionates, methylenebis-b-hydroxynaphthoates, gentisic acid, isethionates, di-p-toluoyltartrates, methanesulfonates, ethanesulfonates, benzenesulfonates, p-toluenesulfonates, cyclohexyl sulfamates and quinateslaurylsulfonate salts, and the like. (See, for example, S. M. Berge et al. "Pharmaceutical Salts" *J. Pharm. Sci*, 66: p. 1-19 (1977) which is incorporated here by reference).

In a preferred embodiment, said compound of formula (I) is riluzole (which is represented by formula (II) above). By "riluzole", we mean 2-amino-6-trifluoro-methoxy-benzothiazole, as well as its pharmaceutically acceptable salts. Riluzole can, for example, be prepared according to the method described in patent EP 0 050 551. The use of riluzole for the treatment of neurodegenerative pathologies is, for example, described in U.S. Pat. No. 6,872,739 and patent application EP 0 558 861.

In a preferred embodiment of the invention, the anticancer agent is a platinum salt. Platinum salts are commonly used in the treatment of cancer. However, platinum salts induce numerous adverse effects, including neurotoxicity, myelosuppression, nephrotoxicity, ototoxicity, nausea and vomiting.

In the context of this invention, the adverse effect corresponds preferably to neurotoxicity, which is manifested in particular by hypersensitivity to cold and/or muscle disturbances. However, the adverse effect may correspond to another adverse effect, such as myelosuppression, nephrotoxicity, ototoxicity, nausea or vomiting. A person skilled in the art may refer to Wolf et al., European Journal of Cancer 2008, 44: 1507-1515.

In one embodiment, the adverse effect is hypersensitivity to cold.

The platinum salts used in the treatment of cancers include in particular oxaliplatin (sold under the name Eloxatine©), cisplatin (CDDP, sold under the name Cisplatyl©) and carboplatin (CDCP, sold under the name Paraplatine©). Oxaliplatin, cisplatin and carboplatin are therefore preferred platinum salts according to the invention. In a particularly preferred manner, the platinum salt is oxaliplatin.

Oxaliplatin is in particular used in the treatment of colon cancers, colorectal cancers, ovarian cancers and stomach cancers. Its association with 5-fluoro-uracil and folinic acid is called the FOLFOX protocol. With respect to the other platinum salts, this drug has low hematotoxicity and no renal toxicity. However, it has high neurotoxicity. It is responsible for specific sensory neuropathies, exaggerated by the cold, and of which the severity increases with the cumulative dose.

Cisplatin is the basis of numerous chemotherapy protocols, and is used in particular for the treatment of testicular cancers, prostate cancers, cervical cancers, ovarian cancers, endometrial cancers, lung cancers, bladder cancers, aerodigestive tract cancers, sarcomas and neuroblastomas. Its main toxicities are renal (tubular nephrotoxicity) and neurological (neurotoxicity).

Discovered in 1975, carboplatin has two carboxylate groups instead of the two chlorine atoms for cisplatin. It is used for the treatment of testicular cancers, ovarian cancers, aerodigestive tract cancers and lung caners. By comparison with cisplatin, it has lower renal and neurological toxicity. However, there is a greater risk of bleeding.

The invention also relates to a compound of formula (I), in particular riluzole, for a use in the treatment or prevention of an adverse effect, in particular neurotoxicity, induced by an anticancer agent other than a platinum salt. Indeed, most anticancer agents have adverse effects, and in particular neurotoxicity. As the inventors have demonstrated that a compound of formula (I) is suitable for the treatment and/or prevention of oxaliplatin-induced neurotoxicity, it is possible to deduce that the compound of formula (I) is also suitable for the treatment and/or prevention of neurotoxicity induced by other anticancer agents.

In one embodiment, the adverse effect is hypersensitivity to cold.

By "anticancer agent", we mean here any active principle used for the treatment of cancer. Anticancer agents in particular include alkylating agents, antimetabolites, intercalating agents, mitotic spindle poisons, antitumor antibiotics and modifiers of the tertiary structure of the DNA such as topoisomerase inhibitors.

Preferably, the anticancer agent according to the invention is an anticancer agent that induces neurotoxicity as an adverse effect. This is in particular the case of mitotic spindle poisons, such as *vinca* alkaloids and taxanes.

By "*vinca* alkaloid" or "periwinkle alkaloid", we mean here an alkaloid capable of being extracted from periwinkle (*Vinca rosea* and *Catharanthus roseus*, for example) or an alkaloid derived from same. The *vinca*-alkaloids include vincristine, vinblastine, vindesine and vinorelbine.

By "taxane", we mean here a terpene capable of being extracted from an if (Taxus) or a terpene derived from same. The taxanes include paclitaxel (sold under the name Taxol©) and docetaxel (sold under the name Taxotere).

This is also the case for platinum salts, as mentioned above.

In the context of this invention, the compound of formula (I), more specifically riluzole, is preferably used in combination with the anticancer agent of which it prevents the adverse effects. The administration of the compound of formula (I) and the anticancer agent can be simultaneous or sequential.

The anticancer agent may be present in the same pharmaceutical composition as the compound of formula (I). The invention therefore relates to a pharmaceutical composition containing a pharmaceutically acceptable carrier and, as active principles, a compound of formula (I), more specifically riluzole, as well as an anticancer agent, more specifically a platinum salt. According to one embodiment, the pharmaceutical composition includes riluzole and a platinum salt. According to another embodiment, the pharmaceutical composition includes riluzole and oxaliplatin.

Alternatively, the anticancer agent may be present in a pharmaceutical composition separate from that containing the compound of formula (I). The invention therefore relates to a combination (kit) containing (i) a first pharmaceutical composition containing a pharmaceutically acceptable vehicle and a compound of formula (I); and (ii) a second pharmaceutical composition containing a pharmaceutically acceptable carrier and an anticancer agent. A kit according to the invention may optionally include instructions regarding the mode of administration of the first and the second pharmaceutical composition for the treatment and prevention of a cancer. The use (administration) of the first and second pharmaceutical composition of such a combination (kit) may be simultaneous or sequential. According to one embodiment, the first pharmaceutical composition includes riluzole and the second pharmaceutical composition includes a platinum salt. According to another embodiment, the first pharmaceutical composition includes riluzole and the second pharmaceutical composition includes oxaliplatin.

By "pharmaceutically acceptable carrier", we mean any solvent, dispersion medium, absorption retardant, etc., that does not produce a secondary reaction, for example an allergic reaction, in humans or animals. Pharmaceutically acceptable carriers are well known to a person skilled in the art, and include those described in "Remington's Pharmaceutical Sciences" (Mack Publishing Company, Easton, USA, 1985). The pharmaceutically acceptable carrier is in particular chosen on the basis of the route of administration, which may be, for example, oral, sublingual, nasal, buccal, rectal, parenteral (i.e. intravenous, subcutaneous, intradermal or intramuscular). The route of administration is preferably oral or parenteral. The dose is dependent on factors such as the active principle considered, the mode of administration, the therapeutic indication, and the age, weight and condition of the patient.

Advantageously, the pharmaceutical compositions according to the invention and the combinations (kits) according to the invention are used for the treatment or the prevention of cancer. The cancer may be chosen from testicular cancer, thyroid cancer, ovarian cancer, cervical cancer and/or endometrial cancer, breast cancer, esophageal cancer, bladder cancer, an otorhinolaryngologic (ORL) cancer, lung cancer, stomach cancer, prostate cancer, a sarcoma, a neuroblastoma, colorectal cancer, rectal cancer and colon cancer.

In a preferred embodiment, the pharmaceutical compositions according to the invention and the combinations (kits) according to the invention contain oxaliplatin as a platinum salt, riluzole as a compound of formula (I), and are used for the treatment or prevention of a colorectal cancer. In such pharmaceutical compositions and combinations (kits) according to the invention, riluzole makes it possible to treat or prevent adverse effects, in particular neurotoxicity induced by the antineoplastic agent oxaliplatin.

The invention also relates to a method for treating or preventing an adverse effect induced by an anticancer agent, including the administration of an effective amount of a compound of formula (I), more specifically riluzole, to an individual. This individual can be an individual who has been treated by the anticancer agent, who is being treated by the anticancer agent or who will be treated by the anticancer agent. The different characteristics described above apply to this method. Thus, the anticancer agent can be a platinum salt, in particular oxaliplatin. Thus, as well, the adverse effect can be neurotoxicity, for example hypersensitivity to cold. The individual is preferably a mammal, and more specifically human. The effective therapeutic dose can easily be determined by a person skilled in the art.

The invention also relates to a method for treatment or prevention of a cancer, including the administration of a therapeutically effective amount of a compound of formula (I), more specifically riluzole, in combination with an anticancer agent, more specifically a platinum salt, in particular oxaliplatin, to an individual needing it. According to a characteristic of the invention, the method is a method for treating or preventing of a cancer, combined with a method for treating or preventing an adverse effect associated with the anticancer agent used. By combination with an anticancer agent, it should be understood that the individual may be an individual who has been treated by the anticancer agent, who is being treated by the anticancer agent, or who will be treated by the anticancer agent. The individual is preferably a mammal, and more specifically a human being. The effective therapeutic dose may easily be determined by a person skilled in the art. The different characteristics described above apply to this method. Thus, the anticancer agent can be a platinum salt, in particular oxaliplatin. Thus, as well, the adverse effect can be neurotoxicity, for example hypersensitivity to cold.

Finally, another aspect of the invention concerns a screening method for identifying a compound suitable for the treatment or prevention of an adverse effect induced by an anticancer agent, in which said method includes the following steps:
  a) administering an anticancer agent to a non-human animal model;
  b) administering an anticancer agent and a synthetic riluzole analog to a non-human animal model;
  c) measuring an adverse effect induced by the platinum salt in step (a) and (b);
  d) comparing the adverse effect measured in the presence and in the absence of said synthetic riluzole analog; and, optionally,
  e) sacrificing the animals having been used in steps (a) and (b)

in which the measurement of an adverse effect that is significantly lower in the presence of said synthetic riluzole analog, by comparison with that measured in the absence of said synthetic riluzole analog, indicates that said synthetic riluzole analog is suitable for the treatment or prevention of an adverse effect induced by an anticancer agent.

By "synthetic riluzole analog", we mean a chemical compound derived from riluzole. By riluzole derivative, we mean in particular a compound including the more or less substituted benzothiazole skeleton. Such analogs include, but are not limited to, compounds of formula (I).

Thus, the compounds defined in EP 0 282 971 are considered here to be synthetic analogs, so that the synthetic analog is a compound that satisfies the following formula (III):

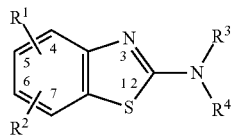

in which:

$R^1$ and $R^2$, which can be identical to or different from one another, represent a hydrogen atom, a linear or branched alkyl radical comprising 1 to 6 carbon atoms, a $C_1$-$C_6$-alkyl-$C_6$-$C_{10}$-aryle radical, a $C_1$-$C_6$-alkenyl or phenyl radical, a $CF_3$ or hydroxy group, a $C_1$-$C_6$-alkoxy, $C_1$-$C_6$-alkylthio or $C_1$-$C_6$-alkylsulfonyl radical, $CF_3O$ in position 6, a halogen atom, a nitro or carboxy group, a $C_1$-$C_6$-alkoxy-carbonyl radical, an $NR^5R^6CO$, $NR^5R^6$, $R^5CONR^5$, CN, or $CR^5R^6SO_2$ group;

in which:

$R^5$ and $R^6$, which may be identical to or different from one another, represent a hydrogen atom, a $C_1$-$C_6$-alkyl radical or a $C_6$-$C_{10}$-aryl radical;

$R^1$ and $R^2$ may together form a carbocyclic or methylenedioxy ring;

$R^3$ represents a hydrogen atom;

$R^4$ represents a hydrogen atom, a $C_1$-$C_6$-alkyl radical, a $C_1$-$C_6$-alkyl radical substituted by a heterocyclic group or a substituted heterocyclic group, a methylcycloalkyl group of which the cycloalkyl part contains up to 6 carbon atoms; a benzyl, phenethyl, phenyl, or substituted phenyl group, a $C_1$-$C_6$-alkyl radical;

propargyl;

with the provisio that $R^1$, $R^2$ and $R^3$ represent hydrogen atoms when $R^4$ is not a hydrogen atom.

Compound III is a derivative selected from the group consisting of:
2-amino-6-methylbenzothiazole,
2-amino-6-trifluoromethoxybenzothiazole,
2-amino-6-trifluoromethylbenzothiazole,
2-aminobenzothiazole,
2-amino-4-methylbenzothiazole,
2-amino-6-ethoxybenzothiazole,
2-amino-6-nitrobenzothiazole,
2-amino-5-methoxybenzothiazole,
2-amino-6-methylsulfonylbenzothiazole,
2-amino-4,6-dimethylbenzothiazole,
ethylaminobenzothiazole,
2-benzylaminobenzothiazole.
2-amino-4-trifluoromethylbenzothiazole,
2-amino-5-trifluoromethylbenzothiazole,
2-amino-6-bromobenzothiazole,
2-amino-6-chlorobenzothiazole,
2-amino-4-chlorobenzothiazole,
2-amino-6-fluorobenzothiazole,
2-amino-5-methoxybenzothiazole,
2-amino-4,6-difluorobenzothiazole,
2-amino-6-methylthiobenzothiazole,
2-amino-naphtho[1,2-d]thiazole, and
2-[[2-(1-methyl-2-pyrrolidinyl)ethyl]amino]-benzothiazole.

The adverse effect measured in the context of the screening method according to the invention can, for example, correspond to neurotoxicity, myelosuppression, nephrotoxicity, ototoxicity, nausea or vomiting induced by a platinum salt. In a preferred embodiment of the invention, the adverse effect is neurotoxicity. In a preferred embodiment of the invention, the adverse effect is hypersensitivity to cold.

The neurotoxicity induced by a platinum salt may, for example, be measured as described in example 2, by measuring the effect of the compound of formula (I) on the hypersensitivity to cold induced by a platinum salt in a rat as an animal model. Animal models enabling the neurotoxicity induced by a taxane or by vincristine are known in the field, and can also be used (Authier et al., Brain Res. 2000 291: 73-76; Authier et al., Neurotherapeutics. 2009 6: 620-629; Authier et al., Neurotoxicology. 2003 24: 797-805).

The following examples and figures show the invention without limiting its scope.

EXAMPLES

Example 1

Protocols 1.1. Animals

Male Sprague-Dawley rats (Charles River Lab, France), weighing 175 to 200 grams, were placed in a cage with food and water ad libitum, in a temperature-controlled environment at 22° C. with a 12 h/12 h day/night cycle. The experiments were conducted under blind conditions in a calm room by the same experimenter, while taking care to comply with the regulations on animal experimentation.

1.2. Molecules

The following molecules were used: riluzole (Sigma Chemical Co., St Louis, Mo.) and oxaliplatin (Debiopharm, Lausanne, Switzerland). The riluzole was prepared in NaCl (0.9%). The oxaliplatin was diluted in a glucose solution (5%).

1.3. Model of Chemo-Induced Neurotoxicity with Oxaliplatin in the Rat

Each rat received, intraperitoneally (IP), a either a dose of oxaliplatin or a glucose 5% control injection. The behavioral test, the immersion of the rat's tail in water at 10° C., was performed before and 72 hours after the injection of the oxaliplatin or the carrier. Then, the riluzole, at doses of 2.5, 5 or 7.5 mg/kg, or its carrier, was administered subcutaneously and the animals were again tested according to the following kinetics: at 15, 30, 45, 60, 90, and 120 minutes after injection of the riluzole or carrier.

1.4. Test of Immersion of the Rat's Tail into Water at 10° C.

This low-temperature immersion test made it possible to measure the hypersensitivity to cold in the animals. The bottom third of the rat's tail was immersed in a temperature-controlled bath 10° C. until it was removed or until the "cut-off" set at 30 seconds (Necker and Hellon. 1978 Pain. 4: 231-242).

1.5. Statistical Analyses

The experimental data was analyzed using the software program Sigma STAT, version 3.0 for Windows (STAT32 Software Inc., San Diego, Calif.). The kinetics of the reaction times to the temperature-based stimulation were analyzed using a two-factor variance analysis followed by a multiple comparison test to study the change over time. The scores of the groups treated with riluzole and the control groups were compared by a student test t. The significance threshold was $P<0.05$.

Example 2

Figure 1:
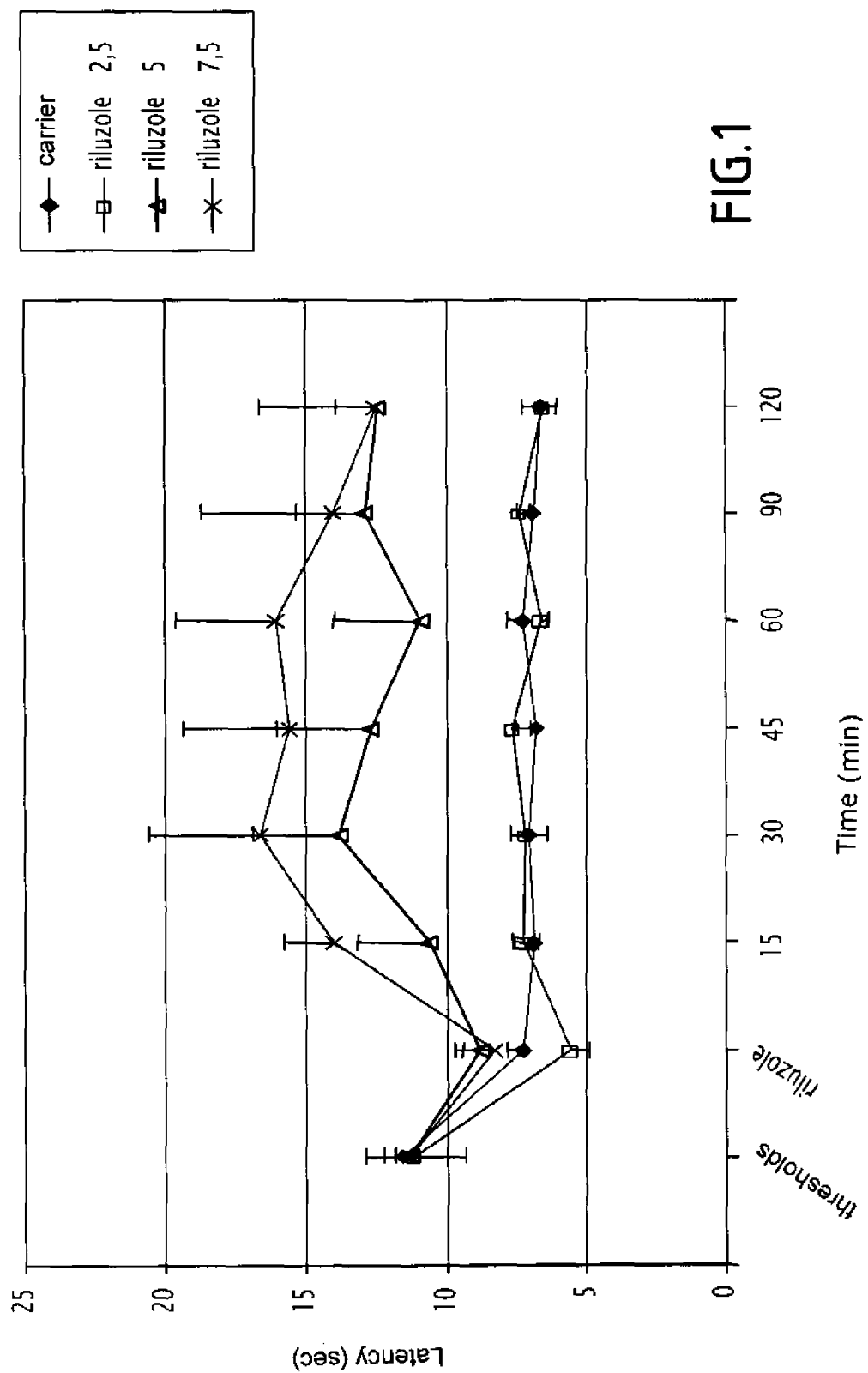
FIGS. 1 and 2 show that riluzole is capable of correcting hypersensitivity to cold induced by an oxaliplatin injection.

Effect of Riluzole on Cold Sensitivity in the Rat Suffering from Oxaliplatin-Induced Neurotoxicity The effects of the three doses of riluzole (2.5, 5 and 7.5 mg/kg) injected intraperitoneally were tested using the temperature-based test of immersion of the tail in water at 10° C., before and 72 hours after injection of oxaliplatin. The oxaliplatin reduced the cold sensitivity threshold (10° C.) (FIG. 1). The untreated rat removed its tail after around 12 seconds, while the rat treated with oxaliplatin removed its tail after 7 seconds, and this effect persisted throughout the experiment.

Figure 2:
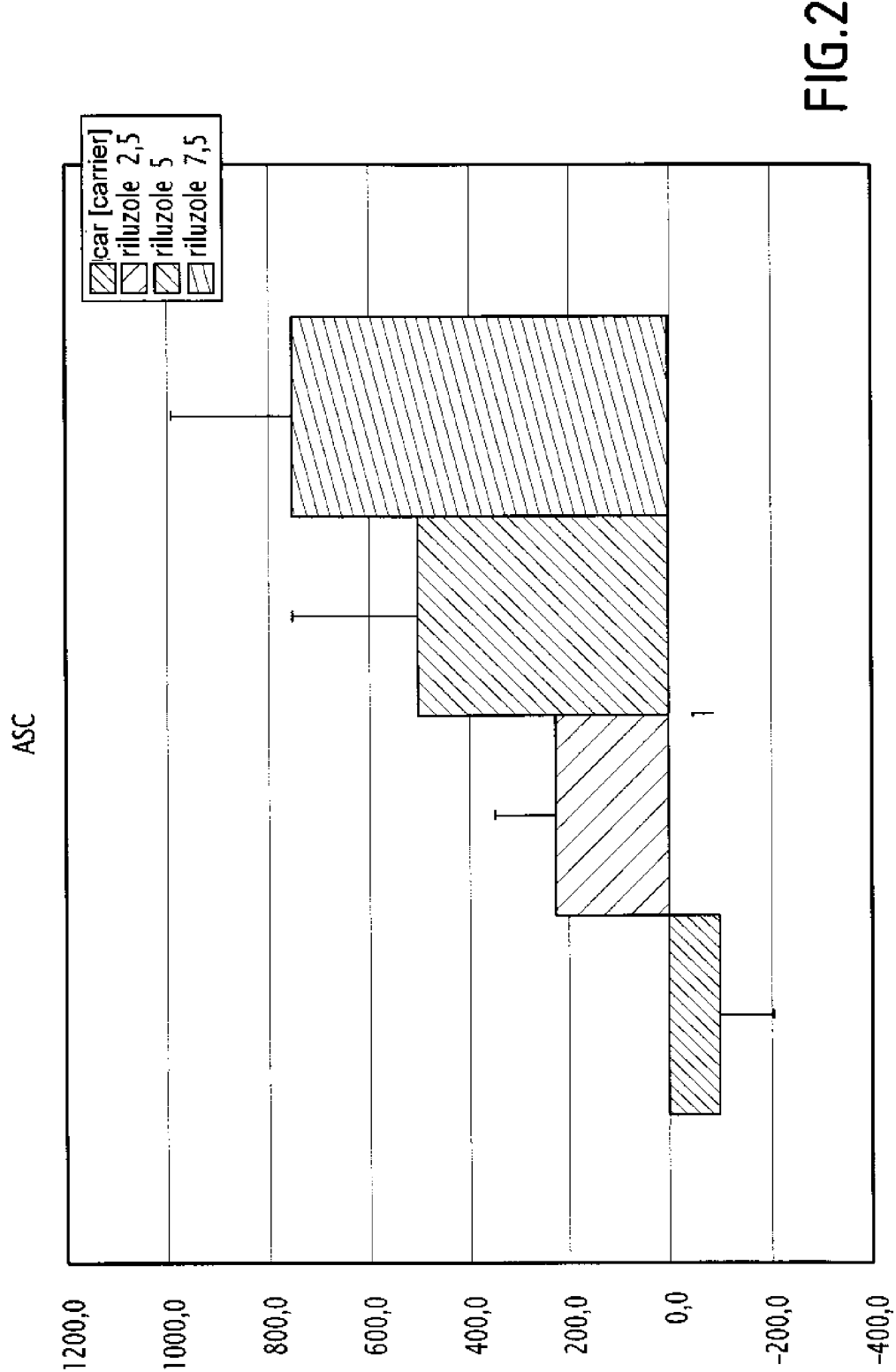

FIG. 1 clearly shows that the reaction times of the rat treated with oxaliplatin are considerably higher after injection of riluzole at a dose of 5 mg/kg. The oxaliplatin animals treated with riluzole even have a higher reaction time to cold (less sensitivity) than that observed before injection of oxaliplatin. The statistical data analysis showed significant differences at doses of 5 mg/kg ($p<0.05$) and 7.5 mg/kg ($p<0.001$) (FIG. 1, FIG. 2).

Example 3

Conclusion

The potential of riluzole to reduce cold hypersensitivity phenomena was evaluated. In an animal model, the rat, riluzole corrected the oxaliplatin-induced cold hypersensitivity. This important effect suggests that riluzole might have a beneficial action on all of the sensory symptoms observed in neurotoxicity associated with the treatment of human pathologies using oxaliplatin.

What is claimed is:

1. A method for treating or reducing an adverse effect induced by an anticancer agent, wherein the adverse effect is chronic neurotoxicity or acute and chronic neurotoxicity, in an individual who has been treated with an anticancer agent, who is being treated with the an anticancer agent, or who will be treated with the an anticancer agent, method comprising:
administering an amount of a compound of formula (I) or a pharmaceutically acceptable salt of formula (I) to the individual effective to treating or reducing said adverse effect induced by the anticancer agent, wherein formula (I) is as follows:

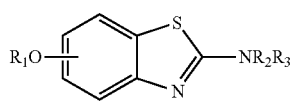

(I)

wherein:
$R_1$ is selected from the group consisting of a hydrogen atom, a $C_1$-$C_6$ alkyl group and a $C_1$-$C_6$ halogenoalkyl group;
$R_2$, $R_3$, identical or different, are selected from the group consisting of a hydrogen atom or a $C_1$-$C_6$ alkyl group.

2. The method of claim 1, further comprising:
administering a therapeutically effective amount of the anticancer agent to the individual prior to, concurrently, or after administering the compound of formula (I).

3. The method of claim 1, in which the acute neurotoxicity induced by the anticancer agent is hypersensitivity to cold.

4. The method of claim 1, in which said anticancer agent is oxaliplatin, cisplatin or carboplatin.

5. The method of claim 1, in which said anticancer agent is oxaliplatin.

6. The method of claim 1, in which said compound of formula (I) is riluzole.

7. The method of claim 2, in which said anticancer agent is oxaliplatin, cisplatin or carboplatin.

8. The method of claim 2, in which said anticancer agent is oxaliplatin.

9. The method of claim 2, in which said compound of formula (I) is riluzole.

10. The method of claim 2, in which said compound of formula (I) has R1 being a perfluoroalkyl group.

11. The method of claim 2, in which said compound of formula (I) has R1, being a trifluoromethyl.

12. The method of claim 1, wherein the adverse effect is cold sensitivity.

13. The method of claim 1, wherein the anticancer agent induces neurotoxicity and hypersensitivity to cold.

14. The method of claim 5, wherein the oxaliplatin induces neurotoxicity and hypersensitivity to cold.

15. The method of claim 1, wherein the amount is about 2.5 mg/kg to about 7.5 mg/kg.

16. A method for treating or reducing an chronic neurotoxicity and acute neurotoxicity in an individual who has been treated with oxaliplatin, who is being treated with oxaliplatin, or who will be treated with oxaliplatin, the method comprising:
administering an amount of a compound of formula (I) or a pharmaceutically acceptable salt of formula (I) to the individual that is effective to treat or reduce the chronic neurotoxicity and acute neurotoxicity in the individual, wherein formula (I) is as follows:

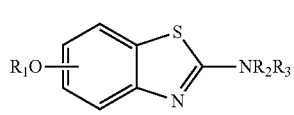

(I)

wherein:
$R_1$ is selected from the group consisting of a hydrogen atom, a $C_1$-$C_6$ alkyl group and a $C_1$-$C_6$ halogenoalkyl group; and
$R_2$, $R_3$, identical or different, are selected from the group consisting of a hydrogen atom and a $C_1$-$C_6$ alkyl group,
wherein the compound of formula (I) is riluzole and the amount is about 7.5 mg/kg or less.

17. The method of claim 16, wherein the amount is about 2.5 mg/kg to about 7.5 mg/kg.

18. The method of claim 1, wherein the anticancer agent is selected from the group consisting of platinum salt, taxane and *vinca* alkaloid.

19. The method of claim 1, wherein the anticancer agent is selected from the group consisting of cisplatin, carboplatin, vincristine, vindesine, vinorelbine, paclitaxel and docetaxel.

* * * * *